US008864816B2

(12) United States Patent
Weber et al.

(10) Patent No.: US 8,864,816 B2
(45) Date of Patent: Oct. 21, 2014

(54) IMPLANTABLE MEDICAL DEVICES INCORPORATING X-RAY MIRRORS

(75) Inventors: Jan Weber, Maastricht (NL); Aiden Flanagan, Co. Galway (IE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 13/419,864

(22) Filed: Mar. 14, 2012

(65) Prior Publication Data

US 2012/0239138 A1 Sep. 20, 2012

Related U.S. Application Data

(60) Provisional application No. 61/452,798, filed on Mar. 15, 2011.

(51) Int. Cl.

| | |
|---|---|
| *A61F 2/06* | (2013.01) |
| *A61L 27/10* | (2006.01) |
| *A61L 29/18* | (2006.01) |
| *A61L 31/02* | (2006.01) |
| *A61L 27/04* | (2006.01) |
| *A61L 31/18* | (2006.01) |
| *G21K 1/06* | (2006.01) |
| *A61F 2/915* | (2013.01) |

(52) U.S. Cl.
CPC .............. *A61L 31/18* (2013.01); *A61L 27/10* (2013.01); *A61F 2002/91575* (2013.01); *A61L 29/18* (2013.01); *A61L 31/026* (2013.01); *A61L 27/04* (2013.01); *G21K 1/062* (2013.01); *A61F 2/915* (2013.01); *A61L 31/022* (2013.01)
USPC ........ 623/1.15; 623/1.34; 623/1.44; 623/1.46

(58) Field of Classification Search
USPC .............................. 623/1.15, 1.34, 1.44, 1.46
See application file for complete search history.

(56) References Cited

U.S. PATENT DOCUMENTS

| 6,638,301 B1 | 10/2003 | Chandrasekaran et al. |
| 6,869,701 B1 | 3/2005 | Aita et al. |
| 2011/0022160 A1 | 1/2011 | Flanagan et al. |

FOREIGN PATENT DOCUMENTS

WO   WO 2008/005524   1/2008

OTHER PUBLICATIONS

Kumagai et al., "Titanium oxide/aluminum oxide multilayer reflectors for "water-window" wavelengths", Applied Physics Letters, 70(18):2338-2340, May 5, 1997.*

(Continued)

*Primary Examiner* — David Isabella
*Assistant Examiner* — Dinah Baria
(74) *Attorney, Agent, or Firm* — Fish & Richardson P.C.

(57) ABSTRACT

An implantable medical device includes a radiolucent member provided with an x-ray mirror that reflects incident x-ray radiation to enable visualization of the device. The x-ray mirror includes a multilayer nanolaminate having alternating layers of a first metal or ceramic layer deposited by atomic layer deposition having a first refractive index, and a second metal or ceramic layer deposited by atomic layer deposition having a second refractive index that is different from the first refractive index. The nanolaminate includes a total of at least four layers.

27 Claims, 5 Drawing Sheets

(56) References Cited

OTHER PUBLICATIONS

Kim et al., "Titania Nanostructures Fabricated by Atomic Layer Deposition Using Spherical Protein Cages", Langmuir Letter, 25(23):13284-13289, 2009.*

Fabreguette et al., "Ultrahigh x-ray reflectivity from $W/Al_2O_3$ multilayers fabricated using atomic layer deposition," *Appl. Phys. Lett.*, 88:013166 (2006).

Fabreguette et al., "X-ray mirrors on flexible polymer substrates fabricated by atomic layer deposition," *Thin Solid Films*, 515:7177-7180 (2007).

Finch et al., "Biocompatibility of atomic layer-deposited alumina thin films," *J Biomed Mater Res A*. 87(1):100-106 (2008).

George, "Atomic layer deposition: an overview," *Chem. Rev.*, 110(1):111-131 (2010).

Szeghalmi et al., "All dielectric hard x-ray mirror by atomic layer deposition," *Appl. Phys. Lett.*, 94:133111 (2009).

International Search Report and Written Opinion for PCT/US2012/028996, mailed Aug. 2, 2012, 12 pages.

International Preliminary Report on Patentability issued on Sep. 26, 2013 by the WIPO in international application No. PCT/US2012/028996, filed on Mar. 14, 2012, 10 pages.

\* cited by examiner

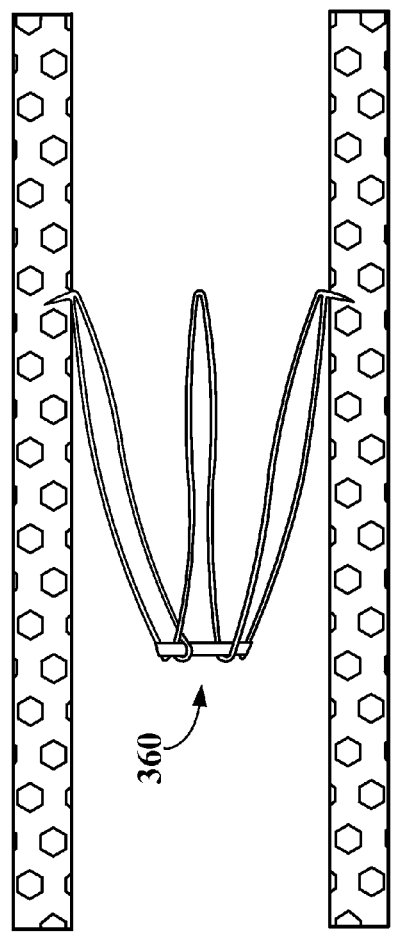
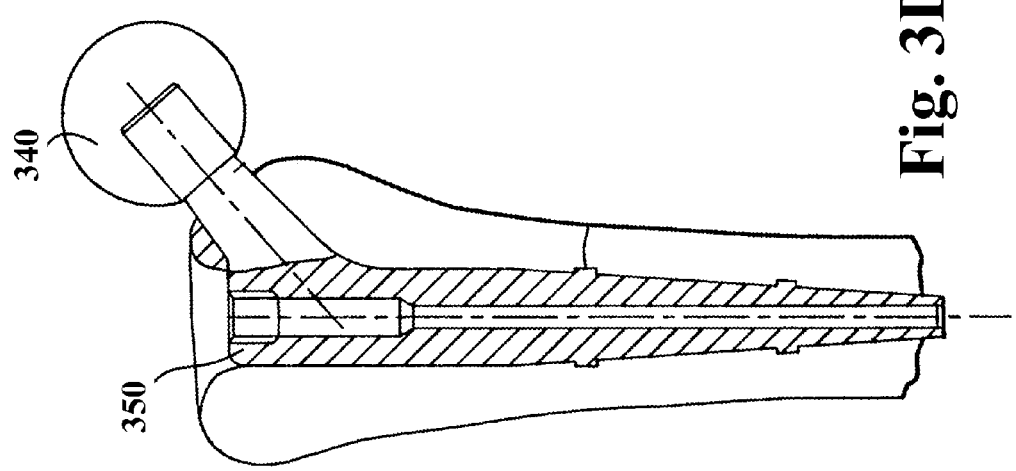
Fig. 3E
Fig. 3D

IMPLANTABLE MEDICAL DEVICES INCORPORATING X-RAY MIRRORS

CLAIM OF PRIORITY

This application claims priority under 35 USC §119(e) to U.S. Provisional Application Ser. No. 61/452,798, filed on Mar. 15, 2011, the entire contents of which are hereby incorporated by reference.

TECHNICAL FIELD

This invention relates to visualizing implantable medical devices.

BACKGROUND

Implantable medical devices include devices such as stents and stent grafts, vascular grafts and valves, heart valves, artificial hearts, joint and bone implants, vascular filters, and the like. In order to locate the implant accurately both during and after implantation, it is important to be able to visualize the implant using non-invasive methods such as x-ray detection. This, in turn, requires that the implant itself be radiopaque. Although some materials such as cobalt-chromium alloys are both suitable for implants and absorb x-rays, rendering them inherently radiopaque, many others are not. In particular, bioerodible materials such as polymers, iron, or magnesium that would otherwise be suitable are radiolucent, rather than inherently radiopaque. Moreover, ultrathin implants may be radiolucent even if they include heavy elements that would otherwise render them radiopaque because the x-ray attenuation length is not sufficiently long. To address this issue, a number of solutions have been proposed, including forming alloys that include one or more x-ray absorbing elements (e.g., platinum, gold, or palladium), and providing the implants with x-ray absorbing markers.

SUMMARY

There is described an implantable medical device that includes a radiolucent member provided with an x-ray mirror that reflects incident x-ray radiation. As used herein, a "radiolucent member" is a member that exhibits a transmission of at least 95% when exposed to x-rays having an energy of 80 keV. The incident radiation may have a wavelength between 0.1 and 10 nm ("soft x-rays") or between 0.01 and 0.10 nm ("hard x-rays"). Detecting the reflected x-ray radiation enables visualization of the implant both during and after implantation. In some embodiments, the x-ray mirror can have a reflectivity of at least 90% at an incident x-ray radiation wavelength of 0.154 nm (Cu Kα wavelength).

The x-ray mirror includes a multilayer nanolaminate having alternating layers of a first metal or ceramic layer deposited by atomic layer deposition having a first refractive index, and a second metal or ceramic layer deposited by atomic layer deposition having a second refractive index that is different from the first refractive index. The nanolaminate includes a total of at least four layers. As used herein, the term "nanolaminate" refers to layered structures in which the individual layers have thicknesses on the order of nanometers.

Examples of suitable metals and ceramics for the individual layers of the nanolaminate include $Al_2O_3$, $SiO_2$, $Si_3N_4$, $TiO_2$, BN, ZnO, W, $IrO_x$, $B_2O_3$, $CO_2O_3$, $Cr_2O_3$, $Fe_2O_3$, $Ga_2O_3$, $HfO_2$, $In_2O_3$, MgO, $Nb_2O_5$, NiO, Pd, Pt, $SnO_2$, $Ta_2O_5$, $TaN_x$, TaN, AlN, $TiCrO_x$, TiN, $VO_2$, $WO_3$, ZnO, (Ta/Al)N, (Ti/Al)N, (Al/Zn)O, ZnS, ZnSe, ZrO, $Sc_2O_3$, $Y_2O_3$, $Ca_{10}(PO_4)(OH)_2$, rare earth oxides, and combinations thereof. In some embodiments, one of the layers may be $Al_2O_3$, $TiO_2$, W, or $Ta_2O_5$. Specific examples of useful nanolaminates include structures in which (a) one layer is $Al_2O_3$ and the other layer is $Ta_2O_5$; (b) one layer is $Al_2O_3$ and the other layer is W; and (c) one layer is $Al_2O_3$ and the other layer is $TiO_2$. In some embodiments, the x-ray mirror may include a smoothing layer between the radiolucent member and the nanolaminate to reduce optical imperfections that might interfere with x-ray reflectivity.

The x-ray mirror may have a total thickness that ranges from about 8 nm to about 5 μm. In some embodiments, the thicknesses of the individual layers of the nanolaminate may vary to form a thickness gradient in the thickness direction of the nanolaminate. The total number of layers in the nanolaminate is chosen to optimize the reflectance angle (i.e. to produce detectable x-ray reflections at a variety of incident angles) and the intensity of the reflected signal. In some embodiments, the total number of layers is at least 8 or at least 10. In some embodiments, the total number of layers is greater than 1,000.

Examples of suitable implantable medical devices include stents and stent grafts, vascular grafts and valves, heart valves, artificial hearts, joint and bone implants, and vascular filters. In the case of stents, the radiolucent member can be a band, connector, or combination of the two.

The radiolucent member may include a polymer, or a metal or metal alloy. For example, the radiolucent member may include a bioerodible metal or metal alloy such as magnesium and alloys thereof, or iron and alloys thereof. In some embodiments, the radiolucent member can include a therapeutic agent.

In some embodiments, the radiolucent member includes an abluminal surface and an adluminal surface, and the x-ray mirror is provided on the abluminal surface. In other embodiments, the x-ray mirror is provided on the adluminal surface. The x-ray mirror may integral with a surface of the radiolucent member (i.e. formed directly on the radiolucent member), or it may be in the form of a separate film that is affixed (e.g., using an adhesive) to a surface of the radiolucent member. In still other embodiments, the x-ray mirror may be in the form of particles (e.g., hollow spheres) incorporated on or in a surface of the radiolucent member.

Implantable medical devices incorporating x-ray mirrors may offer one or more of the following advantages. For example, the x-ray mirror may obviate the need to incorporate radiopaque metal elements into the device, thereby expanding the number of materials that could be used for the implantable device. Such materials include bioerodible metals and polymers. The x-ray mirror may enable visualization of the implant during and after implantation. In the case of implants that include bioerodible metals and polymers, it can be used to monitor the decomposition of the implant following implantation. In addition, it is possible to prepare x-ray mirrors that are electrically insulating (e.g., by using ceramic materials as the individual layers). As a result, when the x-ray mirror is used in combination with a bioerodible medical device, the mirror would not interfere with in vivo corrosion of the device.

The use of atomic layer deposition to form the individual layers of the nanolaminate creates very thin, optically smooth layers. The resulting x-ray mirrors are also very thin, making it possible to manufacture implantable devices that have thin members as well. In addition, the number of layers and thicknesses of individual layers can be varied to optimize reflection intensity at a variety of incident angles, thereby facilitating detection.

Particles provided with the x-ray mirror can be used to focus x-ray radiation as part of radiotherapy used to treat tumors. The particles can be injected or implanted in a patient on or near a tumor site. The x-ray mirror can focus incident x-ray radiation to minimize damage to healthy tissue near the tumor.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 3A-3E depict examples of suitable implantable medical devices. FIG. 3A depicts an example of a vascular valve. FIG. 3B depicts an example of a heart valve. FIG. 3C depicts an example of an artificial heart. FIG. 3D depicts an example of a bone and joint implant. FIG. 3E depicts an example of a vascular filter. Although FIGS. 3A-3E depict various features that may be found in these types of devices, the details shown in FIGS. 3A-3E are not a part of this disclosure.

Like reference symbols in the various drawings indicate like elements.

DETAILED DESCRIPTION

The invention will be described with reference to a stent as the implantable medical device. However, other implantable medical devices, as described in the Summary of the Invention, are equally suitable.

Figure 1:
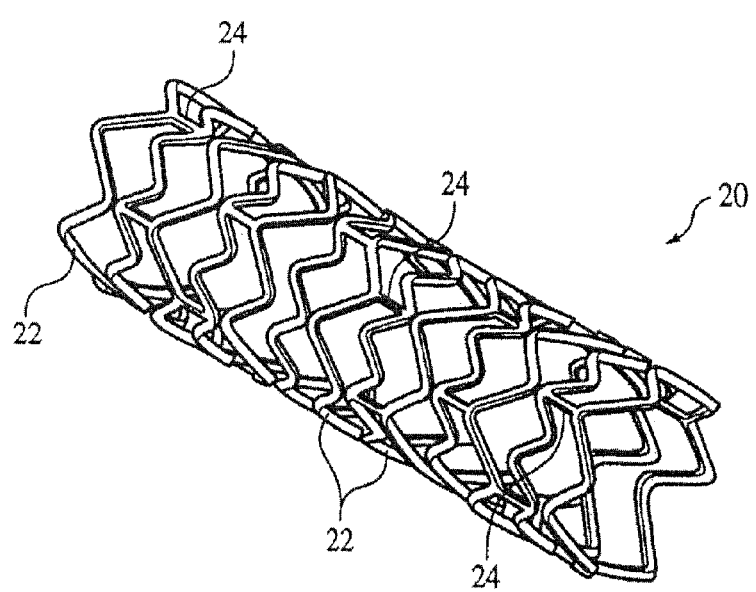
FIG. 1 is a perspective view of a representative implantable medical device in the form of a stent.

As shown in FIG. 1, a stent 20 includes a pattern of interconnected struts forming a structure that contacts a body lumen wall to maintain the patency of the body lumen. For example, stent 20 can have the form of a tubular member defined by a plurality of bands 22 and a plurality of connectors 24 that extend between and connect adjacent bands. During use, bands 22 can be expanded from an initial, small diameter to a larger diameter to contact stent 20 against a wall of a vessel, thereby maintaining the patency of the vessel. Connectors 24 can provide stent 20 with flexibility and conformability that allow the stent to adapt to the contours of the vessel.

Figure 2:
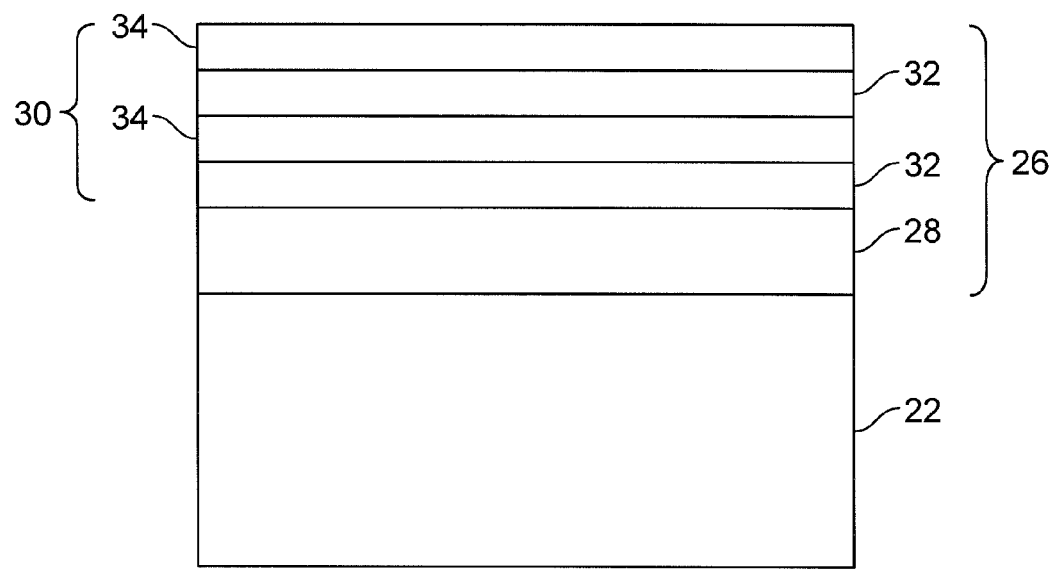
FIG. 2 is a cross-sectional view of a member of the stent shown in FIG. 1, expanded to show an x-ray mirror on the surface of the member.

Referring to FIG. 2, one or more members of stent 20 can be provided with an x-ray mirror 26. In FIG. 2, the stent member is shown as band 22 for ease of illustration; however, other members (e.g., connectors 24) can be provided with an x-ray mirror as well. The member is made of a radiolucent material that, in turn, may be biostable or bioerodible. Examples of biostable, radiolucent materials include stainless steel. Examples of bioerodible, radiolucent materials include iron, magnesium, zinc, tungsten, and alloys of any of these elements with each other or with other elements such as rare earth elements. Representative examples of magnesium alloys include:

(a) a magnesium alloy that includes magnesium, between 7 and 8 weight percent aluminum, between 0.4 and 0.8 weight percent zinc, and between 0.05 and 0.8 weight percent manganese. For example, the bioerodible magnesium alloy can be an AZ80 alloy, which consists essentially of 7.5 weight percent aluminum, 0.5 weight percent zinc, 0.2 weight percent manganese, and a balance of magnesium;

(b) a magnesium alloy that includes less than 5 weight percent (or less than 2 weight percent), in sum, of elements other than magnesium, aluminum, zinc, and manganese. In some embodiments, the bioerodible magnesium alloy can consist essentially of magnesium, aluminum, zinc, and manganese. As used herein, "consisting essentially of" means that the alloy can also include impurities normally associated with the commercially available forms of the constituent elements in amounts corresponding to the amounts found in the commercially available forms of the constituent elements;

(c) a magnesium alloy that includes one or more rare earth metals (e.g., yttrium, neodymium, lanthanum, or cerium). For example, the total amount of rare earth metals within the bioerodible magnesium alloy can be maintained at a level of less than 10.0 weight percent, or less than 2.5 weight percent.

X-ray mirror 26 reflects incident x-ray radiation. The incident x-ray radiation may be in the form of "soft" x-rays (i.e. wavelength ranging from 0.10 to 10 nm) or "hard" x-rays (i.e. wavelength ranging from 0.01 to 0.10 nm). Standard x-ray sources used for medical applications may be used. Detecting the reflected x-ray radiation enables visualization of the stent during and after implantation, despite the fact that the stent itself is formed of radiolucent materials. In the interest of minimizing the overall thickness of the implantable device, the total thickness of x-ray mirror 26 generally will range from about 8 nm to about 5 μm.

X-ray mirror 26 includes a relatively thick "smoothing" layer 28 and a nanolaminate 30 featuring a plurality of thin individual layers 32 and 34 that alternate with each other. The purpose of layer 28, which is optional, is to minimize the optical effects of any imperfections or surface roughness on the surface of the underlying stent member that could interfere with the ability of the mirror to reflect incident x-rays. Typical thicknesses for smoothing layer 28 are on the order of 20-100 nm. The particular material for smoothing layer 28 preferably is the same as one of the materials that form layers 32 and 34. In some embodiments, for example, smoothing layer 28 can include $Al_2O_3$.

Nanolaminate 30 includes a plurality of thin individual layers 32 and 34 that alternate with each other to form a multilayer stack having a total of at least 4 layers. In some embodiments, the nanolaminate can have at least 8 or at least 10 layers. The individual layers may be metal or ceramic layers, with the proviso that within each pair of layers 32, 34, the two layers have different refractive indices from each other. Examples of suitable metals and ceramics for the individual layers of the nanolaminate include $Al_2O_3$, $SiO_2$, $Si_3N_4$, $TiO_2$, BN, ZnO, W, $IrO_x$, $B_2O_3$, $CO_2O_3$, $Cr_2O_3$, $Fe_2O_3$, $Ga_2O_3$, $HfO_2$, $In_2O_3$, MgO, $Nb_2O_5$, NiO, Pd, Pt, $SnO_2$, $Ta_2O_5$, TaN, TaN, AlN, TiCrO, TiN, $VO_2$, $WO_3$, ZnO, (Ta/Al)N, (Ti/Al)N, (Al/Zn)O, ZnS, ZnSe, ZrO, $Sc_2O_3$, $Y_2O_3$, $Ca_{10}(PO_4)(OH)_2$, rare earth oxides, and combinations thereof. In some embodiments, one of the layers may be $Al_2O_3$, $TiO_2$, W, or $Ta_2O_5$. Specific examples of useful nanolaminates include structures in which (a) one layer is $Al_2O_3$ and the other layer is $Ta_2O_5$; (b) one layer is $Al_2O_3$ and the other layer is W; and (c) one layer is $Al_2O_3$ and the other layer is $TiO_2$. The individual layers may be amorphous or crystalline. In some embodiments, x-ray mirror 26 can include multiple stacks of nanolaminates separated from each other by, e.g., polymeric spacer layers.

The total number of layers in the nanolaminate is chosen to optimize the reflectance angle (i.e. to produce detectable x-ray reflections at a variety of incident angles) and the intensity of the reflected signal. In general, the reflectance angle increases as the number of layers decreases, while the signal intensity increases as the number of layers increases. In some embodiments, the total number of layers is no greater than 1,000. In some embodiments, the thicknesses of the individual layers of the nanolaminate may vary to form a thickness gradient in the thickness direction of the nanolaminate.

The layers of the nanolaminate forming the x-ray mirror, as well as the smoothing layer, can be formed by atomic layer deposition. Atomic layer deposition is a self-limiting deposition process in which the growth of the monolayer being deposited stops after a certain point (e.g., because of thermodynamic conditions or the bonding nature of the molecules involved), even though sufficient quantities of deposition materials are still available. Atomic layer deposition creates layers that are optically smooth and uniform, making it particularly suitable for creating the layers of the x-ray mirror.

U.S. Provisional Patent Application 61/228,264, entitled "Medical Devices Having an Inorganic Coating Layer Formed by Atomic Layer Deposition," filed Jul. 24, 2009, which is assigned to the same assignee as the present application and hereby incorporated by reference, describes materials and conditions for using atomic layer deposition to prepare layers on various medical devices. For example, a $TiO_2$ layer can be formed by atomic layer deposition by reacting titanium tetrachloride ($TiCl_4$) and water ($H_2O$) according to the following two sequential half-reactions:

:Mg—OH+$TiCl_4$(g)→:Mg—O—$TiCl_3$+HCl   (A)

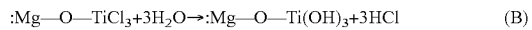

:Mg—O—$TiCl_3$+$3H_2O$→:Mg—O—$Ti(OH)_3$+3HCl   (B)

with :Mg—OH and :Mg—O—$TiCl_3$ being the surface species. These two half-reactions give the overall reaction :Mg—OH+$TiCl_4$+3 $H_2O$→:Mg—O—$Ti(OH)_3$+4 HCl. Titanium tetrachloride and other precursor materials for forming a titanium oxide coating can be obtained from Sigma-Aldrich Corporation of St. Louis, Mo. The choice of deposition temperature is selected based upon the desired crystalline form of the $TiO_2$ layer. The crystalline anatase form of titanium oxide preferentially develops at relatively high deposition temperatures (e.g., greater than 250° C.), whereas the amorphous form of titanium oxide preferentially develops at relatively low deposition temperatures (e.g., less than 150° C.).

Aluminum oxide can be deposited by atomic layer deposition using trimethylaluminum and water as the precursors, and a deposition temperature as low as 50° C. Other examples of suitable reactants and reactant conditions for atomic layer deposition to form layered structures are described, for example, in (a) Fabreguette et al., "X-ray mirrors on flexible polymer substrates fabricated by atomic layer deposition," *Thin Solid Films* 515:7177-7180 (2007); (b) Szeghalmi et al., "All dielectric hard x-ray mirror by atomic layer deposition," *Appl. Phys. Lett.* 94:133111 (2009); and (c) Fabreguette et al., "Ultrahigh x-ray reflectivity from $W/Al_2O_3$ multilayers fabricated using atomic layer deposition," *Appl. Phys. Lett.* 88:013166 (2006).

The x-ray mirror can be provided on all or a portion of the radiolucent member of the implantable medical device. It may be provided on the adluminal or abluminal surface, or both, of an implantable medical device.

The x-ray mirror can be formed directly on the surface of the radiolucent member of the implantable medical device to form a mirror that is integral with the surface. Alternatively, the x-ray mirror can be formed by depositing the individual layers on a separate carrier, e.g., a polymer such as PET or PEN. The resulting sheet can be scribed, e.g., using an ultraviolet laser, to form individual chips or patches on the carrier. The individual chips or patches can then be incorporated in the implantable device, e.g., by adhering the chip or patch to the surface of the device using an adhesive. The carrier can be removed, if desired, by oxidizing or dissolving it.

As shown in FIGS. 1 and 2, the x-ray mirror can be provided in the form of a layered structure on a surface of the implantable medical device. In other embodiments, the x-ray mirror can be provided on a particle. The particles can then be incorporated on or in the surface of the implantable medical device. For example, the particles could be combined with a coatable carrier and then coated onto a surface of the implantable medical device.

The particles can assume a variety of shapes and configurations. For example, the particles could be in the form of solid beads or hollow spheres. Because the layers of the x-ray mirror curve around the surface of spherical particles, the resulting implantable medical device can be visualized regardless of the angle of incidence of the x-rays. To form the particles, the individual layers can be deposited on the surface of a particle, e.g., a polystyrene particle, using atomic layer deposition. If hollow spheres are desired, the polystyrene core could then be removed, e.g., by oxidation.

By incorporating the particles on a surface of a bioerodible implantable device, the particles remain after the bioerodible portions have degraded. Thus, the x-ray mirror-bearing particles could be used to monitor the degradation of the implant, as well as the condition of the area of the implant. For example, in the case of stents, the particles could be used to monitor the vascular passage into which the stent had been implanted to look for signs of restenosis.

The x-ray mirror-bearing particles could also be injected or implanted in a patient undergoing radiation treatment. The particles could focus the incident x-ray radiation to minimize damage to surrounding tissue.

The implantable medical device can optionally include a therapeutic agent. The therapeutic agent may be any pharmaceutically acceptable agent (such as a drug), a biomolecule, a small molecule, or cells. Exemplary drugs include anti-proliferative agents such as paclitaxel, sirolimus (rapamycin), tacrolimus, everolimus, biolimus, and zotarolimus. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, lipids, and compounds have a molecular weight of less than 100 kD. Exemplary cells include stem cells, progenitor cells, endothelial cells, adult cardiomyocytes, and smooth muscle cells.

The therapeutic agent can be combined with a polymer to control the release rate of the drug. A barrier layer can also be used for controlling the release of the therapeutic agent.

A number of embodiments of the invention have been described. Nevertheless, it will be understood that various modifications may be made without departing from the spirit and scope of the invention. Accordingly, other embodiments are within the scope of the following claims.

Figure 3A:
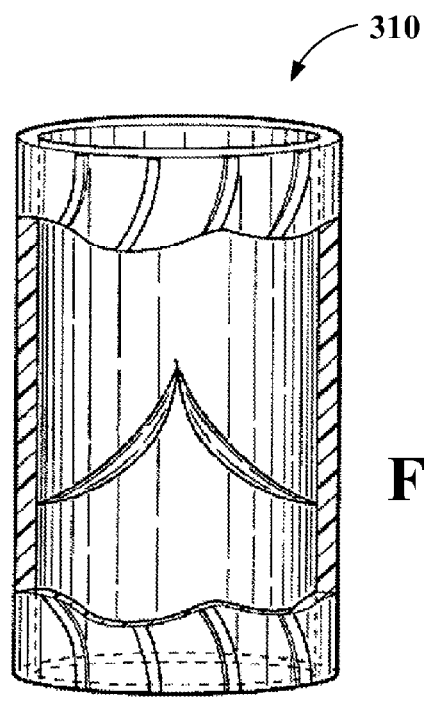
Figure 3B:
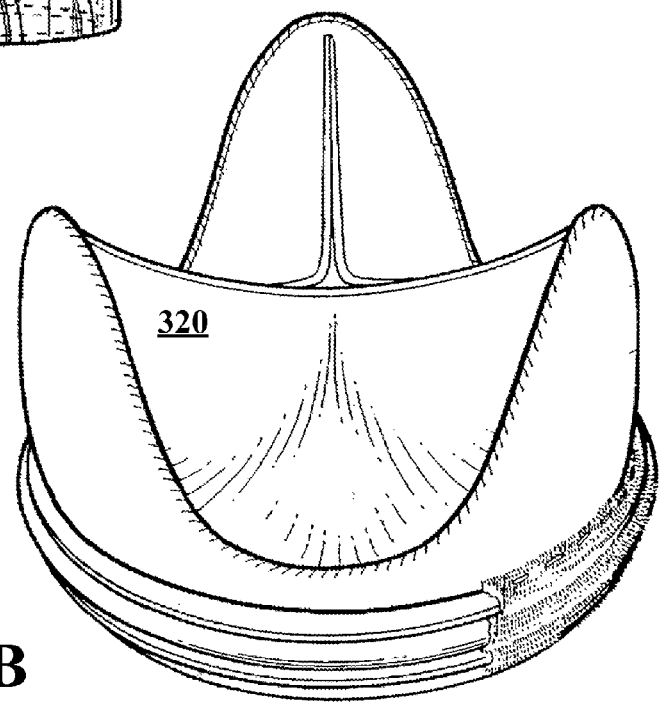
Figure 3C:
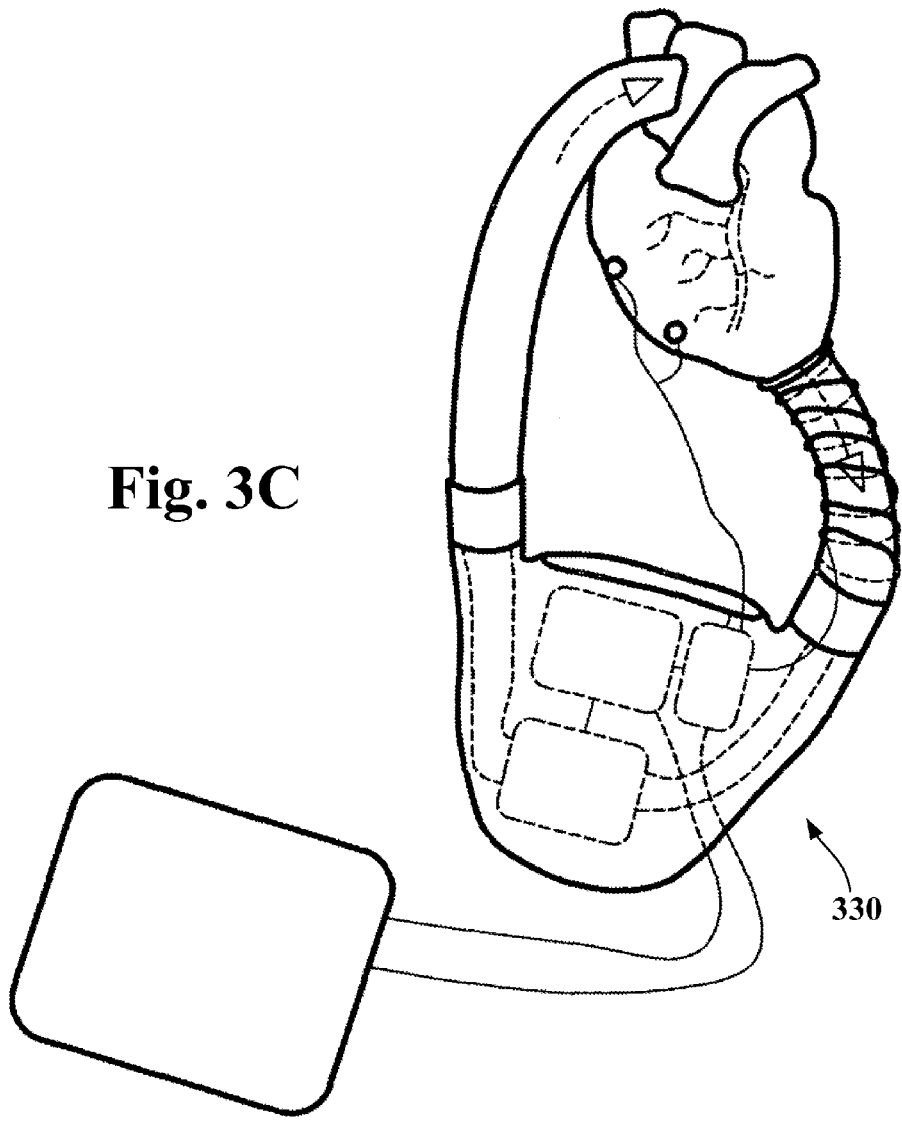

Examples of other suitable implantable medical devices include vascular valves such vascular valve 310 depicted in FIG. 3A, heart valves such heart valve 320 depicted in FIG. 3B, artificial hearts such artificial heart 330 depicted in FIG. 3C, joint and bone implants such joint implant 340 and bone implant 350 depicted in FIG. 3D, and vascular filters such vascular filter 360 depicted in FIG. 3E.

What is claimed is:

1. An implantable medical device comprising a radiolucent member provided with an x-ray mirror that reflects incident x-ray radiation,
wherein the x-ray mirror comprises a multilayer nanolaminate that includes discrete alternating layers of a first metal or ceramic layer deposited by atomic layer deposition having a first refractive index and a second metal or ceramic layer deposited by atomic layer deposition having a second refractive index that is different from the first refractive index, and
wherein the nanolaminate includes a total of at least four layers.

2. An implantable medical device according to claim 1 wherein the radiolucent member includes an abluminal surface and an adluminal surface, and the x-ray mirror is provided on the abluminal surface.

3. An implantable medical device according to claim 1 wherein the radiolucent member includes an abluminal surface and an adluminal surface, and the x-ray mirror is provided on the adluminal surface.

4. An implantable medical device according to claim 1 wherein the implantable medical device is selected from the group consisting of stents, stent grafts, vascular grafts, vascular valves, heart valves, artificial hearts, joint and bone implants, vascular filters, and combinations thereof.

5. An implantable medical device according to claim 1 wherein the implantable medical device comprises a stent.

6. An implantable medical device according to claim 5, wherein the stent comprises a radiolucent member selected from the group consisting of bands, connectors, and combinations thereof.

7. An implantable medical device according to claim 1 wherein the x-ray mirror has a reflectivity of at least 90% at an incident x-ray radiation wavelength of 0.154 nm (Cu Kα wavelength).

8. An implantable medical device according to claim 1 wherein the metal and ceramic materials for the first and second layers are selected from the group consisting of Al2O3, SiO2, Si3N4, TiO2, BN, ZnO, W, IrOx, B2O3, Co2O3, Cr2O3, Fe2O3, Ga2O3, HfO2, In2O3, MgO, Nb2O5, NiO, Pd, Pt, SnO2, Ta2O5, TaNx, TaN, AN, TiCrOx, TiN, VO2, WO3, ZnO, (Ta/Al)N, (Ti/Al)N, (Al/Zn)O, ZnS, ZnSe, ZrO, Sc2O3, Y2O3, Ca10(PO4)(OH)2, rare earth oxides, and combinations thereof.

9. An implantable medical device according to claim 1 wherein one of the first layer or the second layer comprises Al2O3.

10. An implantable medical device according to claim 1 wherein one of the first layer or the second layer comprises TiO2.

11. An implantable medical device according to claim 1 wherein one of the first layer or the second layer comprises W.

12. An implantable medical device according to claim 1 wherein one of the first layer or the second layer comprises Ta2O5.

13. An implantable medical device according to claim 1 wherein the nanolaminate comprises alternating layers of Al2O3 and Ta2O5.

14. An implantable medical device according to claim 1 wherein the nanolaminate comprises alternating layers of Al2O3 and W.

15. An implantable medical device according to claim 1 wherein the nanolaminate comprises alternating layers of Al2O3 and TiO2.

16. An implantable medical device according to claim 1 wherein the radiolucent member comprises a metal or metal alloy.

17. An implantable medical device according to claim 16 wherein the radiolucent member comprises a bioerodible metal or metal alloy selected from the group consisting of Mg, Mg alloys, Fe, Fe alloys, and combinations thereof.

18. An implantable medical device according to claim 1 wherein the radiolucent member comprises a polymer.

19. An implantable medical device according to claim 1 wherein the x-ray mirror is integral with a surface of the radiolucent member.

20. An implantable medical device according to claim 1 wherein the x-ray mirror is in the form of film affixed to a surface of the radiolucent member.

21. An implantable medical device according to claim 1 wherein the x-ray mirror has a total thickness that ranges from about 8 nm to about 5 μm.

22. An implantable medical device according to claim 1 wherein the x-ray mirror comprises a smoothing layer interposed between the radiolucent member and the nanolaminate.

23. An implantable medical device according to claim 1 wherein the total number of layers in the nanolaminate is at least 8.

24. An implantable medical device according to claim 1 wherein the total number of layers in the nanolaminate is at least 10.

25. An implantable medical device according to claim 1 wherein the total number of layers in the nanolaminate is no greater than 1,000.

26. An implantable medical device according to claim 1 wherein the radiolucent member further comprises a therapeutic agent.

27. A stent comprising a radiolucent member selected from the group consisting of bands, connectors, and combinations that comprises a bioerodible metal or metal alloy selected from the group consisting of Mg, Mg alloys, Fe, Fe alloys, and combinations thereof, and is provided with an x-ray mirror that reflects incident x-ray radiation,
wherein the x-ray mirror comprises a multilayer nanolaminate that includes alternating layers of a first layer comprising Al2O3 deposited by atomic layer deposition having a first refractive index, and a second metal or ceramic layer selected from the group consisting essentially of W, Ta2O5, TiO2, and combinations thereof deposited by atomic layer deposition having a second refractive index that is different from the first refractive index, and
wherein the nanolaminate includes a total of at least 10 layers.

* * * * *

UNITED STATES PATENT AND TRADEMARK OFFICE
CERTIFICATE OF CORRECTION

PATENT NO. : 8,864,816 B2  Page 1 of 1
APPLICATION NO. : 13/419864
DATED : October 21, 2014
INVENTOR(S) : Jan Weber and Aiden Flanagan It is certified that error appears in the above-identified patent and that said Letters Patent is hereby corrected as shown below:

In the Claims

In Column 7 Line 42 Claim 8, delete "AN," and insert --AlN,--, therefor.

Signed and Sealed this
Eleventh Day of August, 2015

Michelle K. Lee
*Director of the United States Patent and Trademark Office*